(12) United States Patent
Steinke

(10) Patent No.: US 11,305,123 B2
(45) Date of Patent: Apr. 19, 2022

(54) METHOD AND APPARATUS FOR DETERMINING TOLERANCE THRESHOLDS FOR NEUROSTIMULATION

(71) Applicant: Boston Scientific Neuromodulation Corporation, Valencia, CA (US)

(72) Inventor: G. Karl Steinke, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 431 days.

(21) Appl. No.: 16/151,083

(22) Filed: Oct. 3, 2018

(65) Prior Publication Data

US 2019/0134403 A1    May 9, 2019

Related U.S. Application Data

(60) Provisional application No. 62/583,104, filed on Nov. 8, 2017.

(51) Int. Cl.
*A61N 1/36* (2006.01)
*A61N 1/372* (2006.01)

(52) U.S. Cl.
CPC ..... *A61N 1/36185* (2013.01); *A61N 1/36128* (2013.01); *A61N 1/37247* (2013.01); *A61N 1/36132* (2013.01); *A61N 1/36153* (2013.01); *A61N 1/36157* (2013.01); *A61N 1/36178* (2013.01); *A61N 1/36192* (2013.01); *A61N 1/37241* (2013.01); *A61N 1/37252* (2013.01)

(58) Field of Classification Search
CPC ............ A61N 1/36128; A61N 1/36132; A61N 1/36153; A61N 1/36157; A61N 1/36178; A61N 1/36185; A61N 1/36192; A61N 1/37241; A61N 1/37247; A61N 1/37252
USPC ........................................ 607/1–76, 115–156
See application file for complete search history.

(56) References Cited

U.S. PATENT DOCUMENTS

| | | | |
|---|---|---|---|
| 8,326,433 B2* | 12/2012 | Blum | A61B 34/10 607/59 |
| 8,630,715 B2 | 1/2014 | Goetz et al. | |
| 9,737,717 B2 | 8/2017 | Moffitt et al. | |
| 2015/0088223 A1* | 3/2015 | Blum | A61N 1/37241 607/45 |

(Continued)

*Primary Examiner* — Jonathan T Kuo
*Assistant Examiner* — Vynn V Huh
(74) *Attorney, Agent, or Firm* — Schwegman Lundberg & Woessner, P.A.

(57) ABSTRACT

An example of a system for delivering neurostimulation using a stimulation device and controlling the delivery of the neurostimulation may include a programming control circuit and a stimulation control circuit. The programming control circuit may be configured to program the stimulation device for delivering the neurostimulation according to a pattern of neurostimulation pulses defined by one or more stimulation waveforms. The stimulation control circuit may be configured to determine the pattern of neurostimulation pulses with the one or more stimulation waveforms constrained by one or more thresholds, and may include threshold circuitry that may be configured to receive one or more known values of the one or more thresholds and to determine needed values of the one or more thresholds by executing an algorithm allowing for prediction of the needed values of the one or more thresholds based on the one or more known values.

20 Claims, 9 Drawing Sheets

(56) References Cited

U.S. PATENT DOCUMENTS

| | | |
|---|---|---|
| 2016/0030749 A1* | 2/2016 | Carcieri ............ A61N 1/36128 607/45 |
| 2016/0121126 A1 | 5/2016 | Marnfeldt |
| 2017/0050033 A1 | 2/2017 | Wechter |
| 2017/0106197 A1 | 4/2017 | Wechter et al. |

* cited by examiner

METHOD AND APPARATUS FOR DETERMINING TOLERANCE THRESHOLDS FOR NEUROSTIMULATION

CLAIM OF PRIORITY

This application claims the benefit of priority under 35 U.S.C. § 119(e) of U.S. Provisional Patent Application Ser. No. 62/583,104, filed on Nov. 8, 2017, which is herein incorporated by reference in its entirety.

TECHNICAL FIELD

This document relates generally to medical devices and more particularly to system and method for determining various thresholds for programming parameters of neurostimulation.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform patterns or waveforms continuously or in bursts. However, the human nervous systems use neural signals having much more sophisticated patterns to communicate various types of information, including sensations of pain, pressure, temperature, etc. The nervous system may interpret an artificial stimulation with a simple pattern of stimuli as an unnatural phenomenon, and respond with an unintended and undesirable sensation and/or movement. For example, some neurostimulation therapies are known to cause paresthesia and/or feelings of vibration of non-targeted tissue or organ.

Recent research has shown that the efficacy and efficiency of certain neurostimulation therapies can be improved, and their side-effects can be reduced, by using patterns of neurostimulation pulses that emulate natural patterns of neural signals observed in the human body. This requires various parameters controlling the delivery of the neurostimulation pulses to change dynamically during a therapy session that may last for minutes to hours, depending on each patient's conditions and therapeutic goals.

SUMMARY

An example (e.g., "Example 1") of a system for delivering neurostimulation to tissue of a patient using a stimulation device coupled to a plurality of electrodes and controlling the delivery of the neurostimulation by a user may include a programming control circuit and a stimulation control circuit. The programming control circuit may be configured to program the stimulation device for delivering the neurostimulation according to a pattern of neurostimulation pulses defined by one or more stimulation waveforms. The stimulation control circuit may be configured to determine the pattern of neurostimulation pulses with the one or more stimulation waveforms constrained by one or more thresholds each being a limit for a parameter of waveform parameters defining the one or more stimulation waveforms. The stimulation control circuit may include threshold circuitry that may be configured to receive one or more known values of the one or more thresholds and to determine needed values of the one or more thresholds by executing an algorithm allowing for prediction of the needed values of the one or more thresholds based on the one or more known values.

In Example 2, the subject matter of Example 1 may optionally be configured such that the pattern of neurostimulation pulses includes the one or more stimulation waveforms and one or more stimulation fields each defined by a set of active electrodes through which one or more neurostimulation pulses of the pattern of neurostimulation pulses are delivered to the patient, and the stimulation control circuit includes waveform composition circuitry configured to determine the one or more stimulation waveforms and the one or more stimulation fields.

In Example 3, the subject matter of Example 2 may optionally be configured such that the one or more neurostimulation pulses each have an overall current amplitude, the one or more stimulation fields are each further defined by a fractionalization assigning a fraction of the overall current amplitude to each electrode of the set of active electrodes, and the waveform composition circuitry is further configured to determine the fractionalization for each of the one or more stimulation fields.

In Example 4, the subject matter of any one or any combination of Examples 2 and 3 may optionally be configured such that the threshold circuitry is further configured to receive the one or more known values of the one or more thresholds for each stimulation field of the one or more stimulation fields and to determine the needed values of the one or more thresholds for the each stimulation field.

In Example 5, the subject matter of any one or any combination of Examples 1 to 4 may optionally be configured such that the threshold circuitry is configured to determine one or more thresholds of a first parameter selected from the waveform parameters for one or more given values or one or more value ranges of one or more second parameters selected from the waveform parameters.

In Example 6, the subject matter of Example 5 may optionally be configured such that the threshold circuitry is configured to determine the one or more thresholds of the first parameter for one or more worse-case values of the one or more second parameters.

In Example 7, the subject matter of Example 6 may optionally be configured such that the threshold circuitry is configured to identify one or more worst cases in the pattern of neurostimulation pulses and determine the one or more worse-case values of the one or more second parameters being one or more values of the one or more second parameters under the identified one or more worst cases.

In Example 8, the subject matter of any one or any combination of Examples 6 and 7 may optionally be configured to further include a user interface configured to receive one or more user-defined worst cases in the pattern of neurostimulation pulses from the user and determine the one or more worse-case values of the one or more second parameters being one or more values of the one or more second parameters under the received one or more user-defined worst cases.

In Example 9, the subject matter of any one or any combination of Examples 5 to 8 may optionally be configured such that the first parameter is a pulse amplitude, the second parameter is a pulse width, and the threshold circuitry includes amplitude threshold circuitry configured to determine an amplitude threshold of the one or more thresholds. The amplitude threshold is a limit for the pulse amplitude for each given value or value range of the pulse width.

In Example 10, the subject matter of Example 9 may optionally be configured such that the amplitude threshold circuitry is configured to determine an amplitude threshold of the one or more thresholds. The amplitude threshold is a maximum value of the pulse amplitude for a maximum value of the pulse width in the each given value range of the pulse width.

In Example 11, the subject matter of Example 9 may optionally be configured such that the amplitude threshold circuitry is configured to determine needed values of the amplitude threshold using one or more known values of the amplitude threshold and a relationship between the pulse amplitude and the pulse width.

In Example 12, the subject matter of Example 11 may optionally be configured such that the amplitude threshold circuitry is configured to determine the needed values of the amplitude threshold using the one or more known values of the amplitude threshold and a strength-duration curve.

In Example 13, the subject matter of any one or any combination of Examples 1 to 12 may optionally be configured such that the stimulation control circuit is further configured to control timing of delivery of the pattern of neurostimulation pulses.

In Example 14, the subject matter of any one or any combination of Examples 1 to 13 may optionally be configured such that the stimulation device includes an implantable stimulation device configured to deliver the neurostimulation and to control the delivery of the neurostimulation using a plurality of stimulation parameters.

In Example 15, the subject matter of Example 14 may optionally be configured to further include a programmer including the programming control circuit and the stimulation control circuit. The programming control circuit is configured to generate the plurality of stimulation parameters according to the pattern of neurostimulation pulses and to transmit the plurality of stimulation parameters to the implantable stimulation device.

An example (e.g., "Example 16") of a method for delivering neurostimulation to a patient using a stimulation device coupled to a plurality of electrodes and controlling the delivery of the neurostimulation by a user is also provided. The method may include determining one or more thresholds each being a limit for a parameter of waveform parameters defining one or more stimulation waveforms. This determination may include receiving one or more known values of one or more thresholds and determining needed values of the one or more thresholds by executing an algorithm allowing for prediction of the needed values of the one or more thresholds based on the one or more known values. The method may further include determining the one or more stimulation waveforms using constraints including the determined one or more thresholds, determining a pattern of neurostimulation pulses including the determined one or more stimulation waveforms, and programming the stimulation device for delivering the neurostimulation according to the determined pattern of neurostimulation pulses.

In Example 17, the subject matter of Example 16 may optionally further include determining the one or more known values of one or more thresholds by measuring from the patient.

In Example 18, the subject matter of any one or any combination of Examples 16 and 17 may optionally further include determining the algorithm for the patient using information including data collected from the patient.

In Example 19, the subject matter of any one or any combination of Examples 16 to 18 may optionally further include determining one or more stimulation fields each defined by a set of active electrodes through which one or more neurostimulation pulses of the pattern of neurostimulation pulses are delivered to the patient. The set of active electrodes is selected from the plurality of electrodes. The subject matter of receiving the one or more known values of one or more thresholds as found in any one or any combination of Examples 16 to 18 may optionally include receiving the one or more known values of one or more thresholds for each stimulation field of the one or more stimulation fields. The subject matter of determining the needed values of the one or more thresholds as found in any one or any combination of Examples 16 to 18 may optionally include determining the needed values of the one or more thresholds for the each stimulation field.

In Example 20, the subject matter of determining the one or more stimulation fields as found in Example 19 may optionally include determining a fractionalization for each of the one or more stimulation fields. The one or more neurostimulation pulses each have an overall current amplitude. The one or more stimulation fields are each further defined by a fractionalization assigning a fraction of the overall current amplitude to each electrode of the set of active electrodes. comprises In Example 21, the subject matter of the waveform parameters as found any one or any combination of Examples 19 and 20 may optionally include a pulse amplitude and a pulse width, the subject matter of determining the one or more thresholds as found any one or any combination of Examples 19 and 20 may optionally include determining an amplitude threshold being a maximum value of the pulse amplitude for each given value or range of values of the pulse width.

In Example 22, the subject matter of determining the amplitude threshold as found in any one or any combination of Examples 19 and 20 may optionally include determining a maximum value of the pulse amplitude for a maximum value of the pulse width in the each given range of values of the pulse width.

In Example 23, the subject matter of determining the amplitude threshold as found in any one or any combination of Examples 19 and 21 may optionally include determining needed values of the amplitude threshold using one or more known values of the amplitude threshold and a relationship between the pulse amplitude and the pulse width.

In Example 24, the subject matter of determining the amplitude threshold as found in Example 23 may optionally include determining the needed values of the amplitude threshold using the one or more known values of the amplitude threshold and a strength-duration curve.

In Example 25, the subject matter of Example 24 may optionally further include determining the strength-duration curve for each stimulation field of the one or more stimulation fields using information including data collected from the patient.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
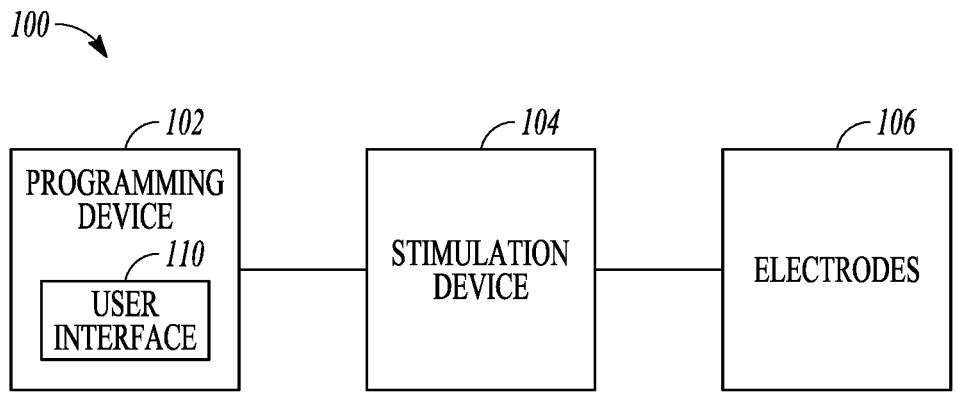
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a method and system for determining tolerance limits for stimulation parameters when programming a stimulation device for delivering neurostimulation to a patient. In various embodiments, the neurostimulation may be delivered as sequenced programs that are not tonic, but include dynamically changing stimulation settings. For example, when the neurostimulation is delivered in a form of electrical pulses, stimulation parameters such as pulse amplitude, pulse width, pulse rate (frequency), and stimulation field (electrode configuration) may change continuously over time. Saving such sequenced programs to the stimulation device (e.g., an implantable pulse generator) of the patient may require setting various thresholds, limits, or set points for each stimulation parameter based on the patient's responses to the neurostimulation. The present subject matter provides for establishing such thresholds. In various embodiments, the present subject matter can facilitate stimulation device programming by ensuring therapy efficacy without consuming excessive energy and/or causing undesirable effects such as patient discomfort, particularly when a sequenced program of neurostimulation is to be programmed. An example of programming sequenced program of neurostimulation is discussed in U.S. Patent Application Publication No. 2017/0050033 A1, entitled "USER INTERFACE FOR CUSTOM PATTERNED ELECTRICAL STIMULATION", assigned to Boston Scientific Neuromodulation Corporation, which is incorporated herein by reference in its entirety.

While simple neurostimulation programs may be tonic with its stimulation parameters remain unchanged with time, sequenced neurostimulation programs with sophisticated patterns of electrical pulses may include dynamic changes of parameters over time durations from microseconds to hours or longer. Throughout each program, the stimulation pulses are to be effective (e.g., evoking tissue responses as intended) while being tolerable to the patient (e.g., not causing pain, sensation, or discomfort to a level that is unacceptable or undesirable the patient, and not causing undesirable effects not sensed by the patient, such as raising blood pressure to an abnormal level). When the patient is allowed to adjust the neurostimulation, often he or she is to be prevented from modifying parameters in a way that can result in uncomfortable or painful stimulation. When the duration of a sequenced program is long (e.g., several minutes or hours), it may be impractical to evaluate all the parameter values in the entire program for the patient. Therefore, the present subject matter checks worst-case settings to establish threshold values for various parameters, such as by prediction, interpolation, and/or extrapolation, thereby eliminating the need to explicitly testing for every needed threshold value. When setting all the parameter values for the worse-case scenario is considered to be over-conservative, the value for a parameter may be set based on testing one or a few scenarios. In some embodiments, this can be done by using one or more known and/or learned relationship between various parameters.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In this document, a "user" includes a physician or other clinician or caregiver who treats the patient using system 100; a "patient" includes a person who receives or is intended to receive neurostimulation delivered using system 100. In various embodiments, the patient can be allowed to adjust his or her treatment using system 100 to certain extent, such as by adjusting certain therapy parameters and entering feedback and clinical effect information.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications, including but not limited to SCS, DBS, PNS, and FES applications. User interface 110 can be configured to allow the user to control the operation of system 100 for neurostimulation.

Figure 2:
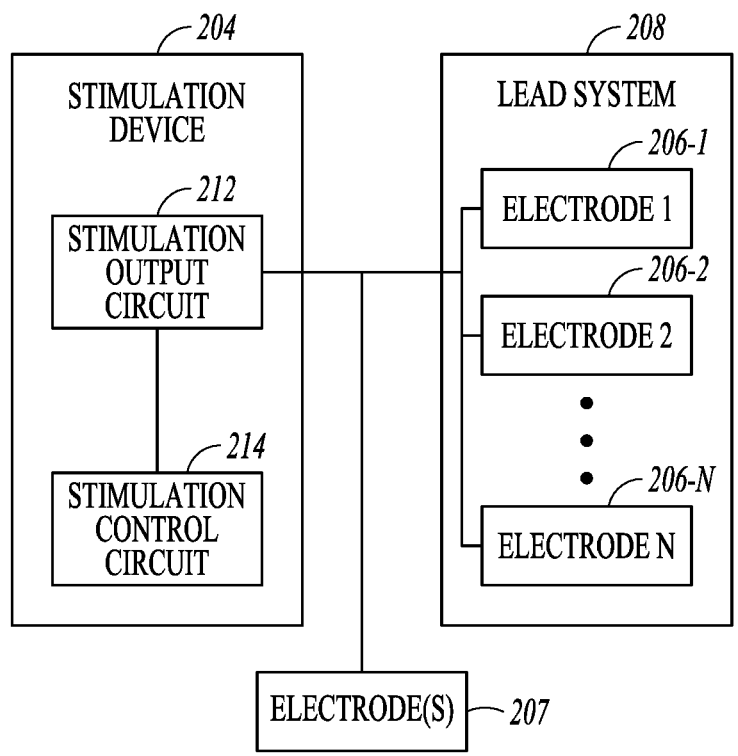
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 can represent an example of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
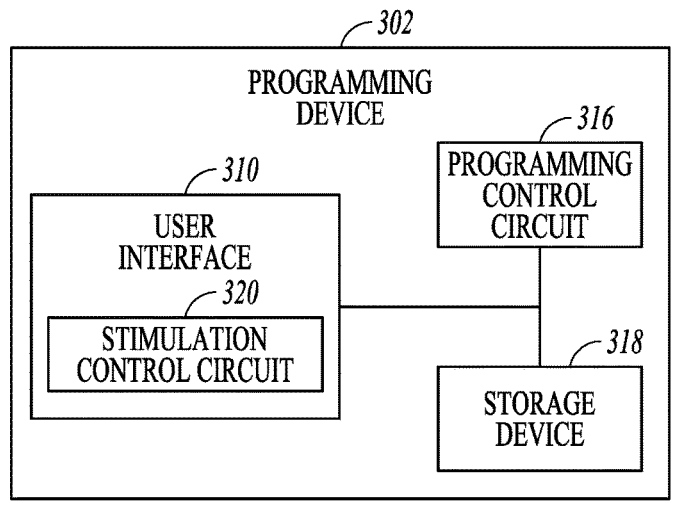
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 can represent an example of programming device 102 and includes a storage device 318, a programming control circuit 316, and a user interface 310. Programming control circuit 316 generates the plurality of stimulation parameters that controls the delivery of the neurostimulation pulses according to a specified stimulation program that can define, for example, stimulation waveform and electrode configuration. User interface 310 can represent an example of user interface 110 and includes a stimulation control circuit 320. Storage device 318 stores information used by programming control circuit 316 and stimulation control circuit 320, such as information about a stimulation device that relates the stimulation program to the plurality of stimulation parameters and information relating the stimulation program to a volume of activation in the patient. In various embodiments, stimulation control circuit 320 can be configured to support one or more functions allowing for programming of stimulation devices, such as stimulation device 104 including but not limited to its various embodiments as discussed in this document.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "stimulation program" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

In various embodiments, circuits of neurostimulation 100, including but not limited to its various embodiments discussed in this document, may be implemented using a combination of hardware and software. For example, the circuit of user interface 110, stimulation control circuit 214, programming control circuit 316, and stimulation control circuit 320, including but not limited to their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
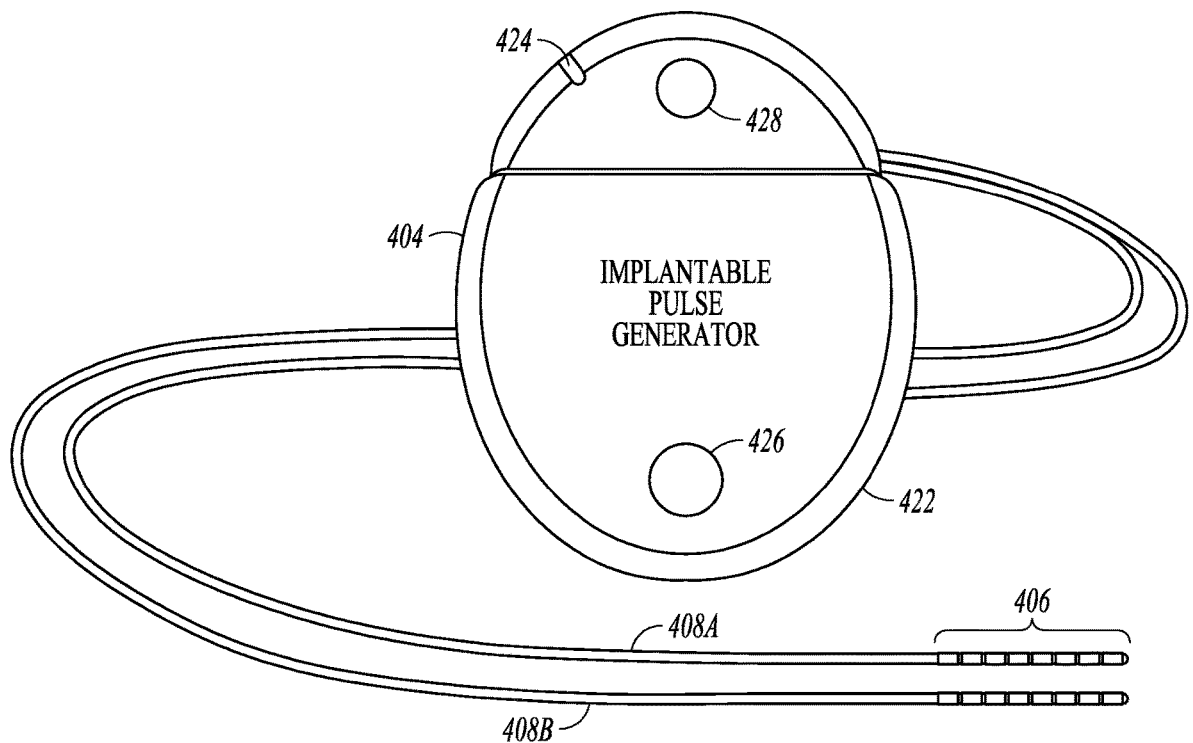
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 4, leads 408A and 408B each include 8 electrodes 406 at the distal end. The number and arrangement of leads 408A and 408B and electrodes 406 as shown in FIG. 4 are only an example, and other numbers and arrangements are possible. In various embodiments, the electrodes are ring electrodes. The implantable leads and electrodes may be configured by shape and size to provide electrical neurostimulation energy to a neuronal target included in the subject's brain, or configured to provide electrical neurostimulation energy to a nerve cell target included in the subject's spinal cord.

IPG 404 can include a hermetically-sealed IPG case 422 to house the electronic circuitry of IPG 404, an electrode 426 formed on IPG case 422, and an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 5:
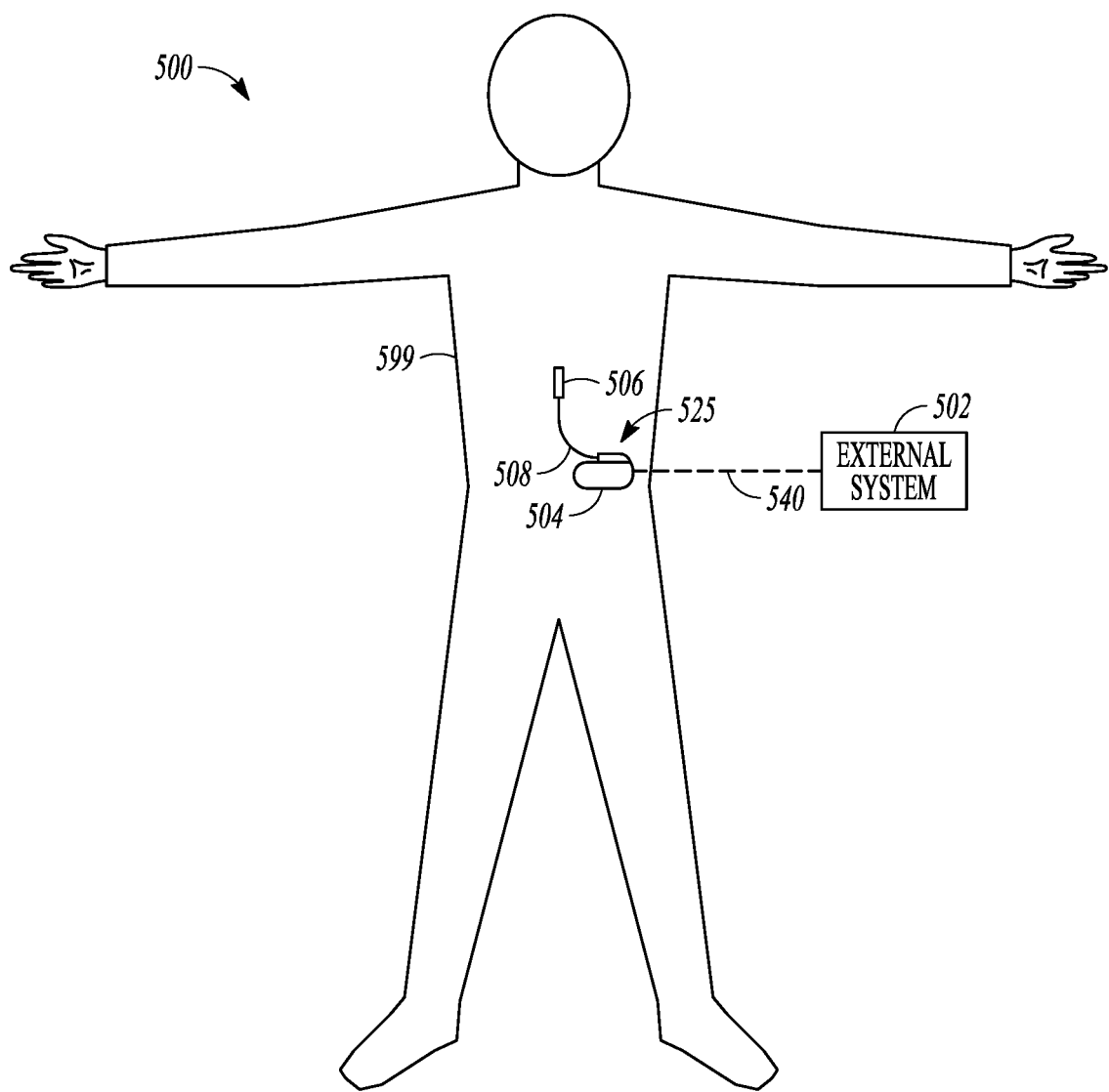
FIG. 5 illustrates an implantable neurostimulation system, such as an example application of the IPG and implantable lead system of FIG. 4, and portions of an environment in which the system may be used.

FIG. 5 illustrates an implantable neurostimulation system 500 and portions of an environment in which system 500 may be used. System 500 includes an implantable system 525, an external system 502, and a telemetry link 540 providing for wireless communication between implantable system 525 and external system 502. Implantable system 525 is illustrated in FIG. 5 as being implanted in the patient's body 599.

An example of IPG 504 includes IPG 404. An example of lead system 508 includes one or more of leads 408A and 408B. In the illustrated embodiment, implantable lead system 508 is arranged to provide SCS to a patient, with the stimulation target being neuronal tissue in the patient's spinal cord. In various embodiments, the present subject matter can be applied to neurostimulation of any types and targets, including but not limited to SCS, DBS, PNS, and FES.

Implantable system 525 includes an implantable stimulator (also referred to as an IPG) 504, a lead system 508, and electrodes 506, which can represent an example of stimulation device 204, lead system 208, and electrodes 206, respectively. External system 502 can represent an example of programming device 302. In various embodiments, external system 502 can include one or more external (non-implantable) devices each allowing the user and/or the patient to communicate with implantable system 525. In some embodiments, external system 502 includes a programming device intended for the user to initialize and adjust settings for implantable stimulator 504 and a remote control device intended for use by the patient. For example, the remote control device may allow the patient to turn implantable stimulator 404 on and off and/or adjust certain patient-programmable parameters of the plurality of stimulation parameters.

The sizes and sharps of the elements of implantable system 525 and their location in body 599 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regarding less of stimulation targets in the patient's body and whether the stimulation device is implantable.

Figure 6:
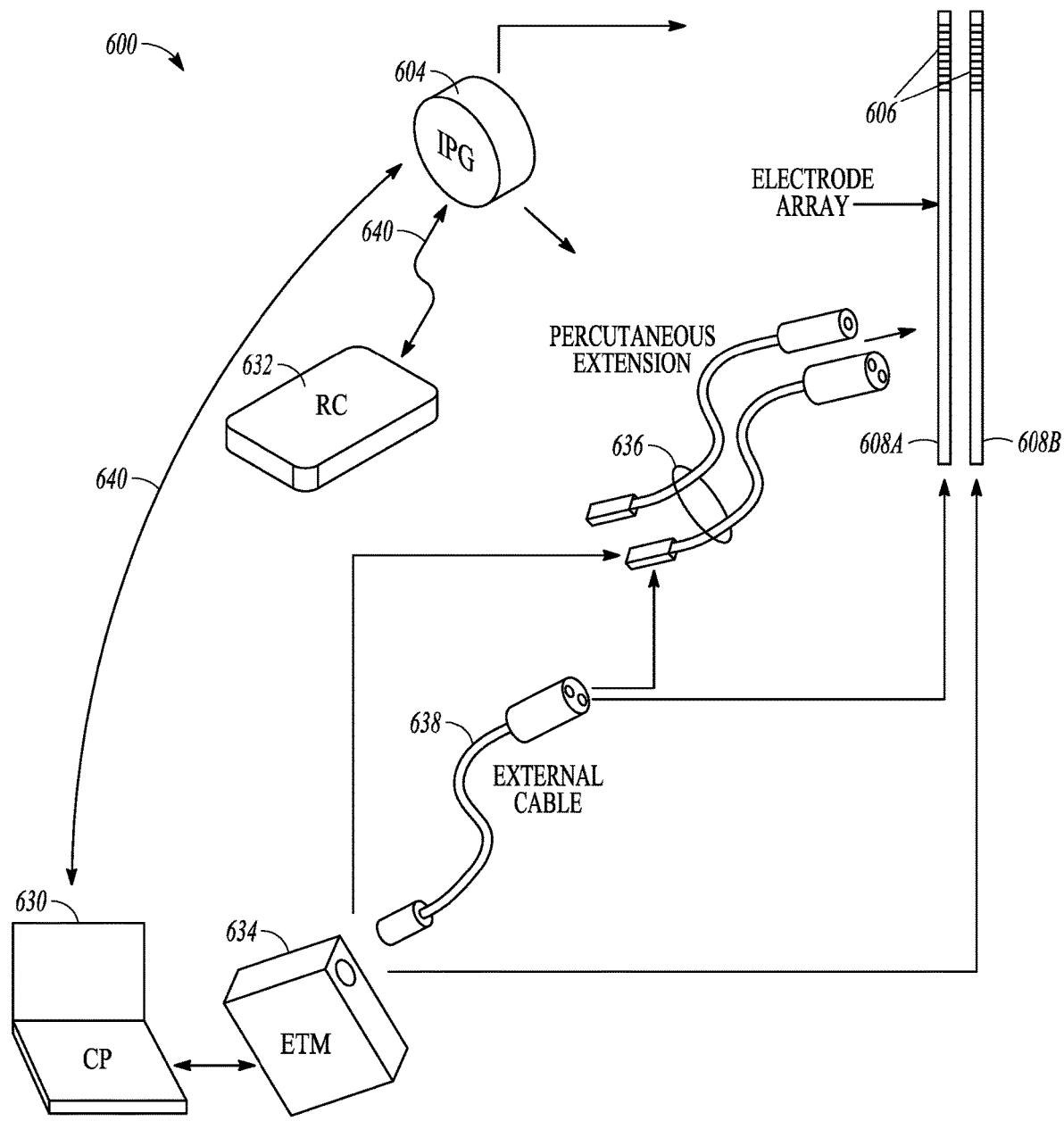
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial modulator (ETM) 634. IPG 404 may be electrically coupled to leads 608A and 608B directly or through percutaneous extension leads 636. ETM 634 may be electrically connectable to leads 608A and 608B via one or both of percutaneous extension leads 636 and/or external cable 638. System 600 can represent an example of system 100, with IPG 604 representing an embodiment of stimulation device 104, electrodes 606 of leads 608A and 608B representing electrodes 106, and CP 630, RC 632, and ETM 634 collectively representing programming device 102.

ETM 634 may be standalone or incorporated into CP 630. ETM 634 may have similar pulse generation circuitry as IPG 604 to deliver neurostimulation energy according to specified modulation parameters as discussed above. ETM 634 is an external device that is typically used as a preliminary stimulator after leads 408A and 408B have been implanted and used prior to stimulation with IPG 604 to test the patient's responsiveness to the stimulation that is to be provided by IPG 604. Because ETM 634 is external it may be more easily configurable than IPG 604.

CP 630 can configure the neurostimulation provided by ETM 634. If ETM 634 is not integrated into CP 630, CP 630 may communicate with ETM 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of r=$\lambda/2\pi$, where $\lambda$ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a pre-programmed stimulation pulse train is applied. RC 632 may be programmed by CP 630. CP 630 may communicate with the RC 632 using a wired or wireless communications link. In some embodiments, CP 630 is able to program RC 632 when remotely located from RC 632.

Figure 7:
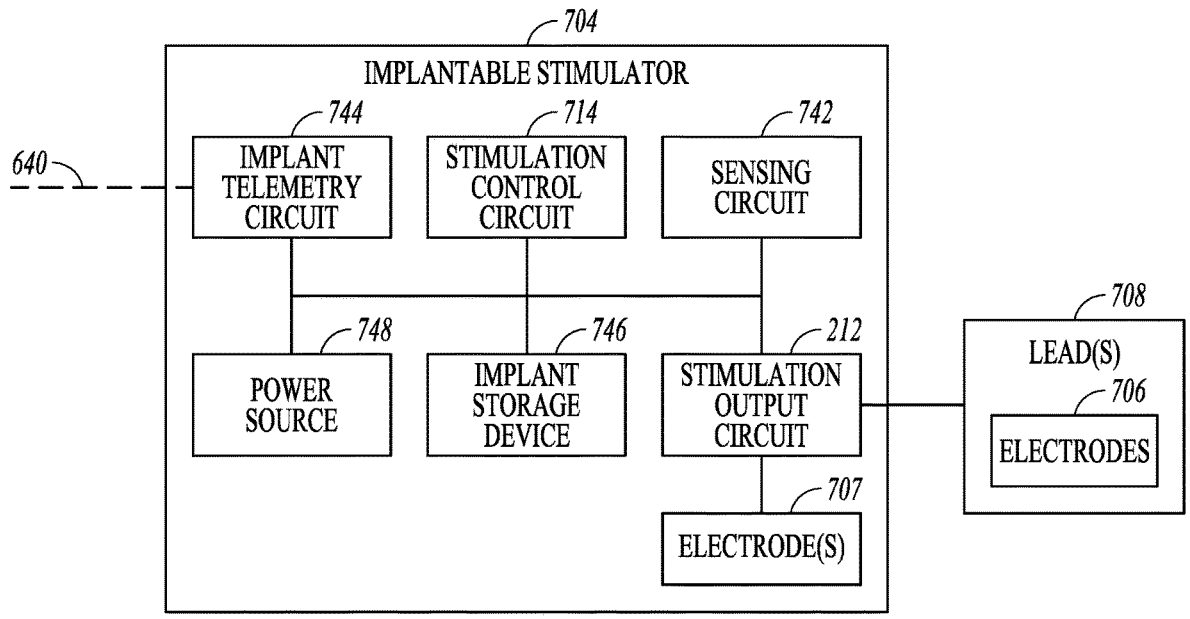
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 can represent an example of stimulation device 104 or 204 and may be implemented, for example, as IPG 404. Lead(s) 708 can represent an example of lead system 208 and may be implemented, for example, as implantable leads 408A and 408B. Lead(s) 708 includes electrodes 706, which can represent an example of electrodes 106 or 206 and may be implemented as electrodes 406.

Implantable stimulator 704 may include a sensing circuit 742 that is optional and required only when the stimulator needs a sensing capability, stimulation output circuit 212, a stimulation control circuit 714, an implant storage device 746, an implant telemetry circuit 744, a power source 748, and one or more electrodes 707. Sensing circuit 742, when included and needed, senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707, and delivers each of the neurostimulation pulses through a set of electrodes selected from electrodes 706 and electrode(s) 707. Stimulation control circuit 714 can represent an example of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 stores values of the plurality of stimulation parameters. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640, and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of postoperative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
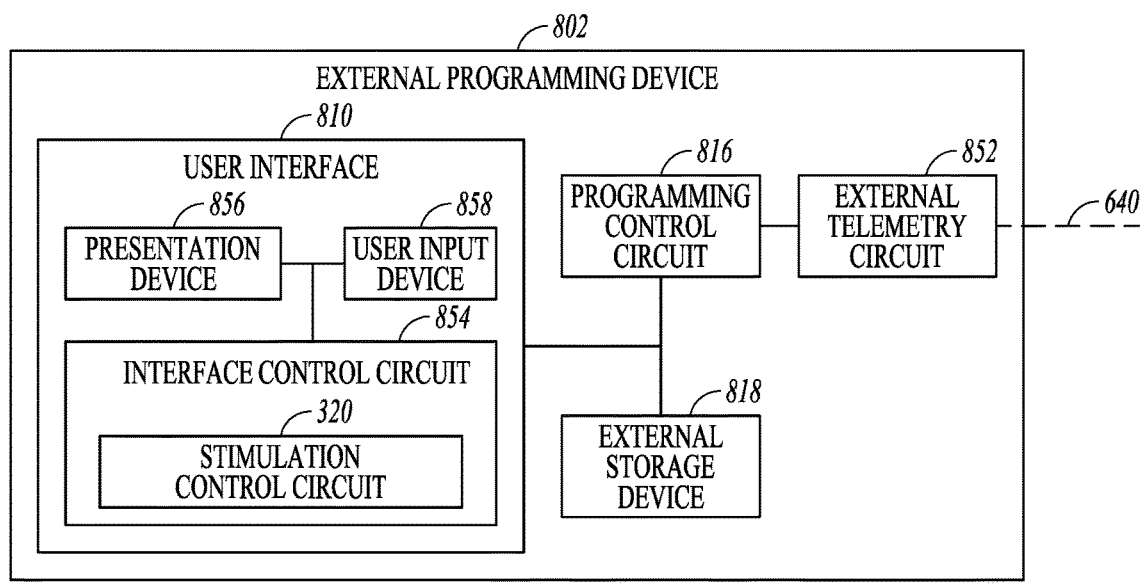
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 can represent an example of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). External telemetry circuit 852 and implant telemetry circuit 744 each include an antenna and RF circuitry configured to support such wireless telemetry.

External storage device 818 stores one or more stimulation waveforms for delivery during a neurostimulation therapy session, as well as various parameters and building blocks for defining the one or more stimulation waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 can represent an example of programming control circuit 316 and generates the plurality of stimulation parameters, which is to be transmitted to implantable stimulator 704, based on a specified stimulation program (e.g., the pattern of neurostimulation pulses as represented by one or more stimulation waveforms and one or more stimulation fields, or at least certain aspects of the pattern). The stimulation program may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 can represent an example of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 includes stimulation control circuit 320.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms, and transmits the plurality of stimulation parameters with the updated values to implantable stimulator 704.

Figure 9:
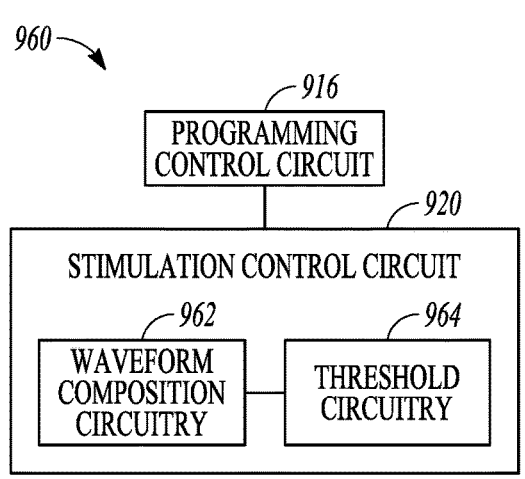
FIG. 9 illustrates an embodiment of a system for determining stimulation parameters that may be implemented as part of the external programming device.

FIG. 9 illustrates an embodiment of a system 960 for determining stimulation parameters. In various embodiments, system 960 may be implemented as part of external programming device 802 (which may be implemented, for example, as CP 630 and/or RC 632) or implemented as any device allowing for determination of stimulation parameters, including any computer programmed for determining stimulation parameters. System 960 can include programming control circuit 816 and stimulation control circuit 920. Programming control circuit 916 can represent an example of programming control circuit 816 and can be configured to program a stimulation device, such as stimulation device 104 including but not limited to its various embodiments as discussed in this document, for delivering neurostimulation according to a pattern of neurostimulation pulses defined by one or more stimulation waveforms. Stimulation control circuit 920 can represent an example of stimulation control circuit 320 and can be configured to determine the pattern of neurostimulation pulses, which is defined by one or more stimulation waveforms. In various embodiments, stimulation control circuit 920 can also schedule deliveries of the neurostimulation according to the pattern of neurostimulation pulses.

Stimulation control circuit 920 can include waveform composition circuitry 962 and threshold circuitry 964. Waveform composition circuitry 962 can determine the one or more stimulation waveforms constrained by one or more thresholds. The one or more thresholds are each being a limit for a parameter of waveform parameters defining the one or more stimulation waveforms. Threshold circuitry 964 can receive one or more known values of the one or more thresholds and determine needed values of the one or more thresholds by executing an algorithm allowing for prediction of the needed values of the one or more thresholds based on the one or more known values. In various embodiments, the one or more known values includes one or more values that can be determined based on data collected from the patient, and the needed values includes all the values needed during determination of the one or more stimulation waveforms. In some embodiments, stimulation control circuit 920 may include threshold circuitry 964 without waveform composition circuitry 962 or a limited version of waveform composition circuitry 962. For example, when system 960 is implemented as part of RC 632 to be given to the patient, RC 632 may only provide the patient with limited control of delivery of the neurostimulation such as to start the delivery, to stop the delivery, and to adjust the intensity of the neurostimulation pulses.

In various embodiments, the pattern of neurostimulation pulses defined by stimulation control circuit 920 can define a stimulation program of a segment of the stimulation program. Programming control circuit 916 can generate a plurality of stimulation parameters according to the pattern of neurostimulation pulses. In embodiments in which programming control circuit 916 is part of a programming device such as external programming device 802, programming control circuit 916 can transmit the plurality of stimulation parameters to implantable stimulator 704 to be used by stimulation control circuit 714 to control delivery of neurostimulation from stimulation output circuit 212. In various embodiments, the pattern of neurostimulation pulses are defined by the one or more stimulation waveforms and one or more stimulation fields. A stimulation program uses multiple stimulation fields if the electrode configuration is to change during the delivery of the neurostimulation according to a pattern of neurostimulation pulses. Each pulse in the pattern of neurostimulation pulses has a stimulation waveform being the waveform of the pulse and a stimulation field specifying electrodes through which the pulse is delivered. The one or more stimulation fields can each be defined by a set of active electrodes through which one or more neurostimulation pulses of the pattern of neurostimulation pulses are delivered to the patient. The set of active electrodes can be selected from a plurality of electrodes such as electrodes 206 and 207, including but not limited to their various embodiments as discussed in this document. In various embodiments, each neurostimulation pulse has an overall current amplitude, and the one or more stimulation fields are each further defined by a fractionalization assigning a fraction of the overall current amplitude to each electrode of the set of active electrodes.

In various embodiments, waveform composition circuitry 962 can determine the one or more stimulation waveforms, including the one or more stimulation fields, that define the pattern of neurostimulation pulses. Examples of waveform composition techniques that may be employed by waveform composition circuitry 1062 include, but are not limited to, those discussed in U.S. Pat. No. 9,737,717, entitled "GRAPHICAL USER INTERFACE FOR PROGRAMMING NEURO STIMULATION PULSE PATTERNS", U.S. Patent Application Publication No. 2016/0121126 A1, entitled "METHOD AND APPARATUS FOR PROGRAMMING COMPLEX NEUROSTIMULATION PATTERNS", U.S. Patent Application Publication No. 2017/0050033 A1, entitled "USER INTERFACE FOR CUSTOM PATTERNED ELECTRICAL STIMULATION", and U.S. Patent Application Publication No. 2017/0106197 A1, entitled "USER INTERFACE FOR NEUROSTIMULATION WAVEFORM COMPOSITION", all assigned to Boston Scientific Neuromodulation Corporation, which are incorporated herein by reference in their entireties.

Threshold circuitry 964 can determine the one or more thresholds for the one or more stimulation waveforms. In various embodiments, threshold circuitry 1064 can receive one or more known values of the one or more thresholds and determine needed values of the one or more thresholds based on the received one or more known values. The one or more known values can be measured, for example, from the patient's response to delivery of neurostimulation pulses according to at least a portion of the pattern of neurostimulation pulses. Threshold circuitry 964 can determine the needed values of the one or more thresholds using the received one or more known values by executing an algorithm allowing for prediction of the needed values of the one or more thresholds based on the one or more known values. In various embodiments, the algorithm can be developed using modeling, pre-clinical data, clinical data, and/or information from literature. When the one or more thresholds relate to pulse amplitude and pulse width, the algorithm can include strength-duration curve fitting.

In various embodiments, threshold circuitry 964 can determine one or more thresholds each being a limit of a waveform parameter for one or more given values or value ranges of other one or more waveform parameters. For example, the waveform parameters can include a pulse amplitude and a pulse width, and threshold circuitry 964 can determine an amplitude threshold being a maximum value of the pulse amplitude for each given value or range of values of the pulse width. This amplitude threshold can be determined for each combination of pulse frequency, pulse shape, and stimulation field used in a stimulation program. While the amplitude threshold will be specifically discussed below as an example, threshold circuitry 964 can determine various types of thresholds for various waveform parameters. Examples of the waveform parameters related to determination of the one or more thresholds by threshold circuitry 964 can include two or more of the following:

(1) pulse amplitude (e.g., amplitude of an electrical current);
(2) pulse width;
(3) pulse frequency (also referred to as pulse rate, stimulation frequency, or stimulation rate, which may also be expressed as inter-pulse interval when referring to an instantaneous rate);
(4) pulse shape (shape or type of the waveform of a neurostimulation pulse, may have a waveform parameter being a quantitative measure of the pulse shape for threshold determination purposes);
(5) stimulation field (may have a waveform parameter being a quantitative measure of the stimulation field for threshold determination purposes); and
(6) pulse charge (for square pulse shapes, the product of pulse amplitude multiplying pulse width, may be used in some embodiments in place of the pulse amplitude and the pulse width for setting the one or more thresholds).

(These examples of waveform parameters are hereinafter referred to as "parameter (1), parameter (2), parameter (3), parameter (4), parameter (5), and parameter (6), respectively.) These parameters are examples of parameters used to quantify the effect on the target tissue, as can be used in the present subject matter, which is not limited by using such parameters. In various embodiments, the present subject matter can work with any parameter used to map to the effect of neurostimulation, such as average power, total electrical energy delivered, etc. Definitions for the amplitude and pulse width may depend on the type (e.g., shape) of the pulse. A square pulse may have a single pulse amplitude across the pulse width. For other pulse shapes, the pulse amplitude may vary across the pulse width, and therefore, the pulse amplitude may include mean, median, mode, peak, and/or minimum amplitudes. In some embodiments, an "equivalent" pulse amplitude may be used to normalize between disparate pulse shapes. For example, a single square wave pulse having a pulse width 100 µs and a pulse amplitude of 5 mA may be used as a normalization target or set point, and a pulse that has, for example, hyperpolarizing pre-pulse of 50 µs followed by a stimulation pulse of again 100 µs may have a peak pulse amplitude of 7 mA but be considered as an equivalent to the square wave pulse having the pulse width 100 µs and the pulse amplitude of 5 mA. Such equivalents of pulse amplitude and pulse width for square wave pulses can be used when the neurostimulation pulses have one or more other pulse shapes. Similarly, for example, pulse frequency can be an average pulse frequency for a given period of time during which the pulse frequency varies to a certain extent. Such variations and equivalencies of parameters apply to each of parameters (1)-(6), with the definitions given in this document being examples.

In various embodiments, threshold circuitry 964 can determine one or more thresholds of a first parameter selected from parameters (1)-(5) for one or more given values or value ranges of one or more second parameters (each being different from the first parameter) selected from parameters (1)-(5). The first parameter may be selected because it has one or more thresholds of interest for ensuring, for example, therapeutic efficacy and/or patient tolerance. The one or more second parameters may each be selected because it can affect the one of more thresholds of the first parameter. When more than one second parameters are selected, threshold circuitry 964 can determine one or more thresholds of the first parameter for one or more given values or value ranges of one of the second parameters while holding the remaining second parameter(s) unchanged when the one or more thresholds are determined for all the interested values or value ranges for this one of the second parameters, and can repeat for each interested combination of values or value ranges of all the second parameters. For example, threshold circuitry 964 can determine one or more thresholds of the pulse amplitude for one or more given values or value ranges of the pulse width for one stimulation field at a time, and repeat until the one or more thresholds of the pulse amplitude are determined for all the stimulation fields. In some embodiments, threshold circuitry 964 can determine one or more thresholds each being a limit of the first parameter being parameter (6) for one or more given values or value ranges of the one or more second parameters selected from parameters (3)-(5).

In various embodiments, threshold circuitry 1064 can determine any type of threshold for a waveform parameter such as one of parameters (1)-(6). Examples of the one or more thresholds that can be determined for each waveform parameter by threshold circuitry 1064 can include one or more of the following:

(A) sufficiency thresholds: a minimum value of a waveform parameter for producing an intended tissue response to the neurostimulation (e.g., activation of a neural target, producing a neural tissue conditioning effect, or producing a desirable sensation); and
(B) excess thresholds: a maximum value of a waveform parameter corresponding to a level of an effect of the neurostimulation that can be harmful to or unacceptable by the patient, with one example being a tolerance threshold being the maximum value of the waveform parameter corresponding to a level of an sensation that can be tolerated by the patient (e.g., pain, undesirable sensation other than pain, or any discomfort). (These examples of thresholds are hereinafter referred to as "threshold (A) and threshold (B), respectively, and each of thresholds (A) and (B) can include one or more thresholds.) In various embodiments, threshold circuitry 964 can determine one or more thresholds selected from thresholds (A) and (B) of the first parameter for one or more given values or value ranges of the one or more second parameters (with the first and second parameters as discussed above).

In some embodiments, threshold circuitry 964 can determine one or more thresholds each being a worst-case limit of the first parameter for one or more worst-case values of the one or more second parameters. The "worst case" can be the worse case for the entire stimulation program or for a portion of the program. Examples for the one or more worst-case values of the one or more second parameters include the highest pulse amplitude, the longest pulse width, the highest pulse frequency, the most efficient stimulation field in producing a response in the patient, the most efficient stimulation field in producing a response in the patient, the most efficient waveform shape in producing a response in the patient, and the largest amount of pulse charge. Because determining a single worst case for an entire stimulation program or an entire pattern of neurostimulation pulses may result in overly conservative thresholds, multiple worst cases can be identified, each from a segment in the pattern of neurostimulation pulses. Threshold circuitry 964 can determine the one or more thresholds for such worst case(s) set by the one or more second parameters. In various embodiments, threshold circuitry 964 can identify such worse case(s) from the one or more stimulation waveforms defining the pattern of neurostimulation pulses and determine the one or more thresholds accordingly. In some embodiments, threshold circuitry 964 can receive user-defined worse case(s) from the user using a user interface, such as user interface 810, and determine the one or more thresholds accordingly. In some embodiments, threshold circuitry 964 can identify worse case(s) from the one or more stimulation waveforms defining the pattern of neurostimulation pulses and receive the user-defined worse case(s) from the user using the user interface, and can determine the one or more thresholds based on both the identified worst case(s) and user-defined worse case(s).

The examples for the waveform parameters and the one or more thresholds, including parameters (1)-(6) and thresholds (A) and (B) are provided for the purpose of illustration, but not for the purpose of restriction. A specific example of using threshold circuitry 964 to determine an amplitude threshold being a maximum value of the pulse amplitude for each given value or range of values of the pulse width is discussed below to illustrate, rather than restrict, how a threshold of a waveform parameter can be determined. This example can be applied for determining one or more thresholds for any waveform parameter, including but not limited to those discussed in this document, by those skilled in the art upon reading and understanding this document.

Figure 10:
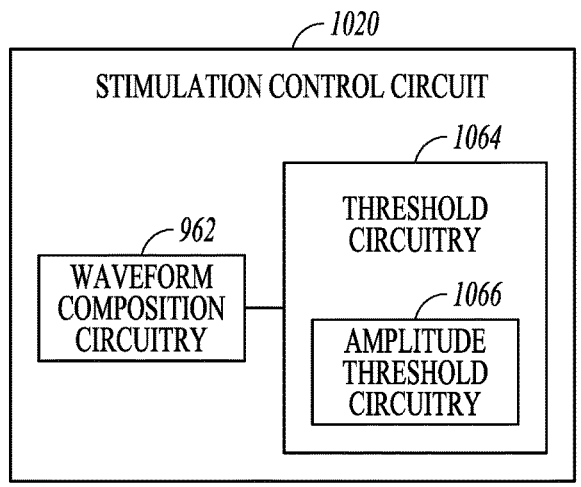
FIG. 10 illustrates an embodiment of a stimulation control circuit of a system for determining stimulation parameters, such as the system of FIG. 9.

FIG. 10 illustrates an embodiment of a stimulation control circuit 1020, which can represent an example of stimulation control circuit 920. Stimulation control circuit 1020 can include waveform composition circuitry 962 and threshold circuitry 1064. Threshold circuitry 1064 can represent an example of threshold circuitry 964. In various embodiments, stimulation control circuit 1020 can determine the pattern of neurostimulation pulses. In various embodiments, stimulation control circuit 1020 can also schedule deliveries of the neurostimulation according to the pattern of neurostimulation pulses.

Each pulse of the pattern of neurostimulation pulses has a value of the pulse amplitude and an associated value of the pulse width. In the illustrated embodiment, threshold circuitry 1064 includes amplitude threshold circuitry 1066 to determine an amplitude threshold being a maximum value of the pulse amplitude for each given value or range of values of the pulse width. In various embodiments, amplitude threshold circuitry 1066 can determine an amplitude threshold for each stimulation field of the one or more stimulation fields associated with the pattern of neurostimulation fields.

In one embodiment, amplitude threshold circuitry 1066 determines an amplitude threshold for a range of values of the pulse width. Amplitude threshold circuitry 1066 can determine the amplitude threshold by measuring the maximum value of the pulse amplitude for a maximum value of the pulse width (e.g., a worst-case value of the pulse width) in the range of values of the pulse width. The range of values of the pulse width can include one or more values of the pulse width. The amplitude threshold can include a plurality of values each being the maximum value of the pulse amplitude for a range of the range of values of the pulse width. Amplitude threshold circuitry 1066 can determine each value of the amplitude threshold by measuring the maximum value of the pulse amplitude for a maximum value of the pulse width in each range of the range of values of the pulse width.

In one embodiment, amplitude threshold circuitry 1066 determines an amplitude threshold using a relationship between values of the pulse amplitude and values of the pulse width. The relationship allows for prediction of values of the amplitude threshold for all the needed values of the pulse width based on one or more values of the amplitude threshold measured for one or more given values of the pulse width. The relationship can be established using data collected from the patient, data collected from a patient population, data resulting from simulations with neurophysiological models, and/or date collected from literature. An example of the relationship includes a strength-duration curve. Amplitude threshold circuitry 1066 can determine each value of the amplitude threshold by measuring one or more maximum values of the pulse amplitude for one or more given values of the pulse width and calculate remaining one or more maximum values of the pulse amplitude using a relationship between the pulse amplitude and the pulse width. In one embodiment, the relationship includes a strength-duration curve. The strength-duration curve can be individually determined for the patient using information including clinical data collected from the patient. When the amplitude threshold needs to be determined for each stimulation field of the one or more stimulation fields associated with the pattern of neurostimulation pulses, the strength-duration curve can also be determined for each stimulation field. Other information such as data collected from a patient population, data resulting from simulation with a neurophysiological model, and/or information from literature may also be used in the determination of the strength-duration curves.

Figure 11:
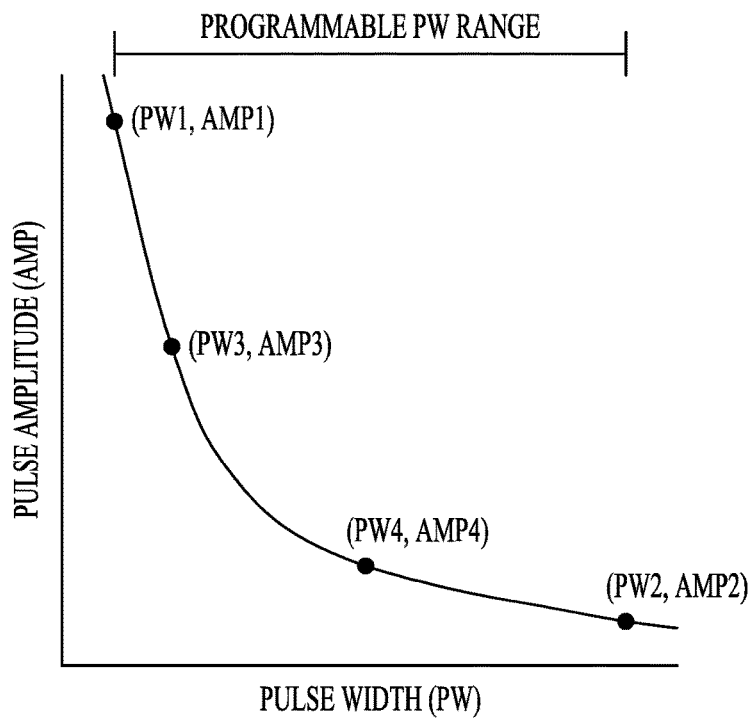
FIG. 11 illustrates an example of a strength-duration curve that can be used by the stimulation control circuit of FIG. 10.

FIG. 11 illustrates an example of a strength-duration curve such as one that can be used by amplitude threshold circuitry 1066. The strength-duration curve is a plot of the pulse amplitude (AMP) versus the pulse width (PW) required to affect in the target tissue of stimulation using electrical pulses as stimuli. In the present subject matter, the strength-duration curve allows for prediction of the pulse amplitude required to produce an effect at each given pulse width. Examples of such an effect can include recruitment (transition between non-excitation to excitation of a neural target as indicated, for example, by evoked action potentials) and onset of pain or other undesirable or desirable sensation.

For the purpose of illustration but not restriction, 4 pairs of known values of the pulse amplitude and the pulse width are shown, including (PW1, AMP1), (PW2, AMP2), (PW3, AMP3), and (PW4, AMP4). In various embodiments, any one or more pairs may be required, and in some embodiments, pairs beyond the required may also be used for additional accuracy, for example. In various embodiments, the values of the pulse width are given, and the value of the pulse amplitude can be made known, for example, by measurement performed on the patient. In the illustrated example, the "PROGRAMMABLE PW RANGE" represents the range of values or the pulse width that may be used in the one or more stimulation waveforms, with PW1 being the minimum value and PW2 being the maximum value. PW3 and PW4 are values that may be arbitrarily chosen or evenly distributed between PW1 and PW2. In various embodiments, one or more AMP-PW pairs may be used for determining the needed values for the amplitude threshold. In one embodiment, one pair such as any of the four illustrated pairs may be required. In another embodiment, two pairs such as the illustrated (PW1, AMP1) and (PW2, AMP2) may be required. In one embodiment, the user may enter as many pairs as desirable when many values of the amplitude threshold are known.

Figure 12:
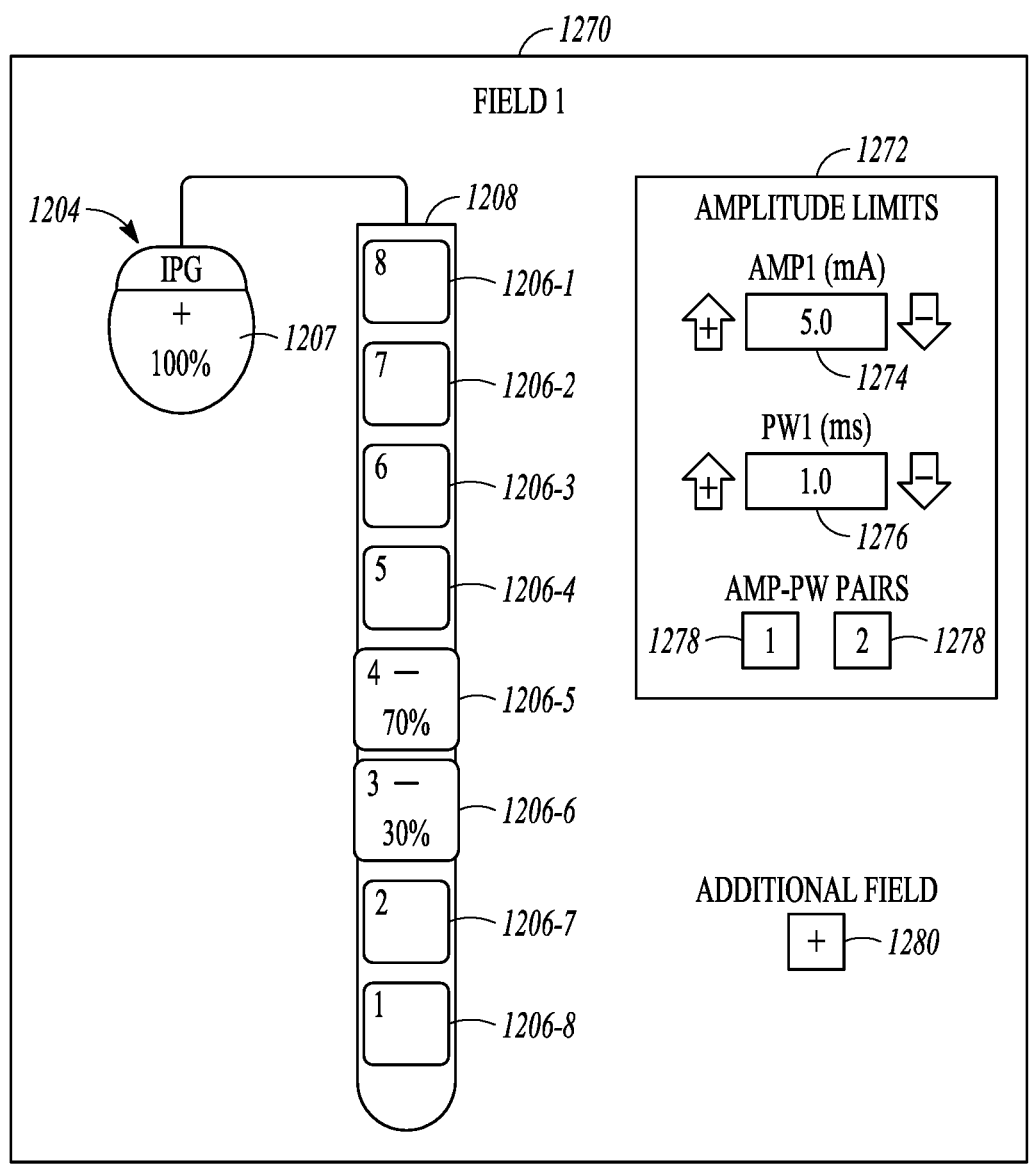
FIG. 12 illustrates an embodiment of an area of a screen of a user interface that may be coupled to the stimulation control circuit of FIG. 10.
Figure 13:
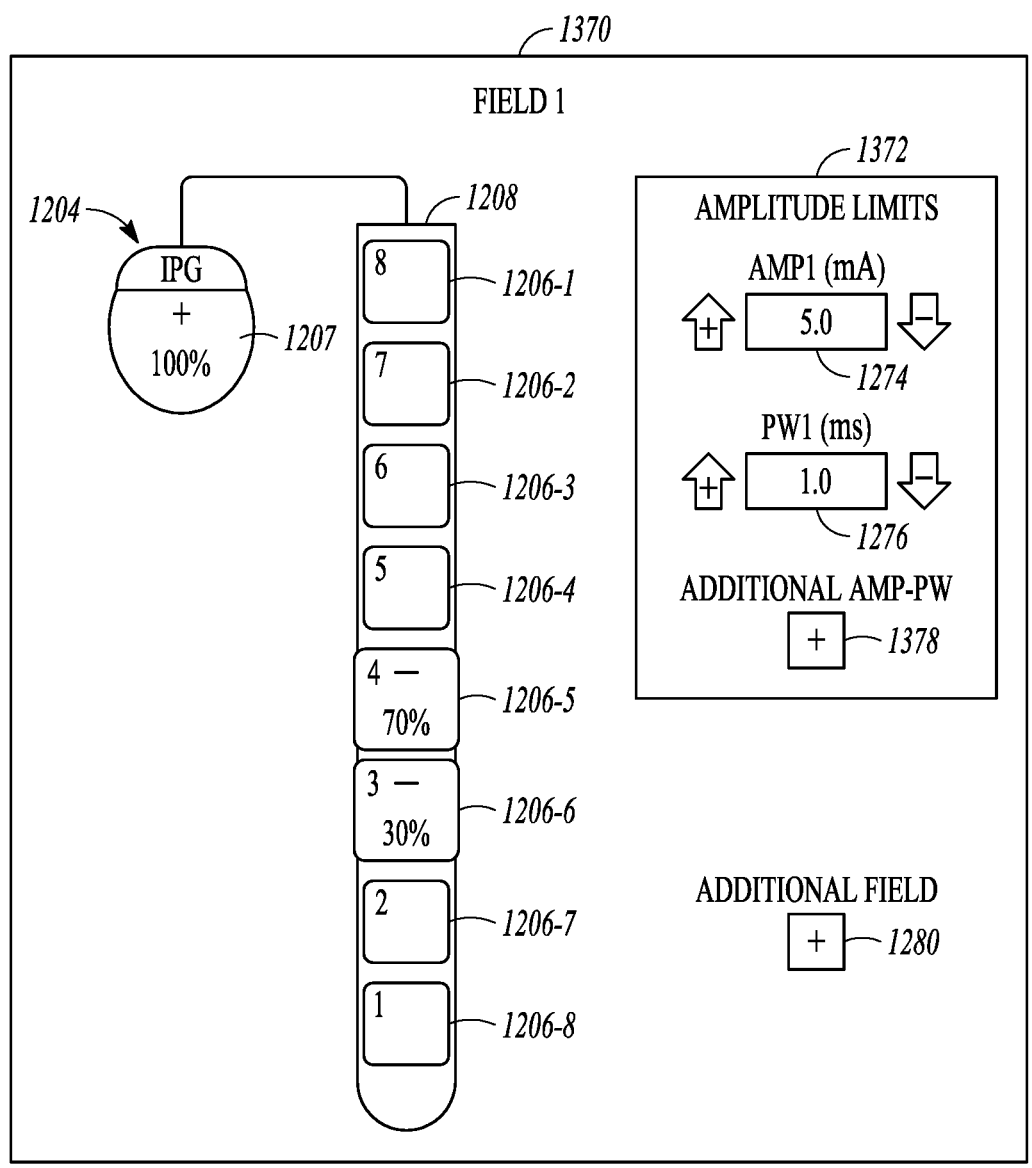
FIG. 13 illustrates another embodiment of an area of the screen of FIG. 12.

FIGS. 12 and 13 illustrate how user may enter the known values of the amplitude threshold. In various embodiments, a user interface such as user interface 810 can receive known values of the amplitude threshold for each stimulation field N of n stimulation fields (N=1, 2, . . . , n). For each stimulation field N, the user interface can display m (m≥1) values of the pulse width and receive a value of pulse amplitude for each value M (M=1, 2, . . . m) of the pulse width. In one embodiment, all of the m values of the pulse width are given (read only to the user). In another embodiment, at least one of the m values of the pulse width are given (read only to the user), the user is allowed to enter more values of the pulse width for which the values of the pulse amplitude are known. In another embodiment, all of the m values of the pulse width and the corresponding m values of pulse amplitude are entered by the user FIG. 12 illustrates an embodiment of an area 1270 of a screen, such as a window, or other portions of a screen of presentation device 856. In various embodiments, presentation device 856 can include a display screen, and area 1270 can be displayed on the screen as a window or a portion of the window. In the illustrated embodiment, area 1270 allows for determining the amplitude threshold for each stimulation field ("FIELD 1" shown as an example). An IPG 1204 includes a housing used as an electrode 1207 and is coupled to a lead 1208 including electrodes 1206-1 through 1206-8. A fractionalization assigns electrode 1207 as a single anode and electrodes 1206-5 and 1206-6 as cathodes with 70% of the overall current amplitude applied to electrode 1206-5 and 30% of the overall current amplitude applied to electrode 1206-6. An AMPLITUDE LIMITS area 1272 presents areas allowing the user to enter known values of the amplitude threshold and the pulse width. In one example, as illustrated in FIG. 12, two pairs of values of the pulse amplitude and the pulse width are to be received from the user. Area 1272 includes AMP-PW PAIRS field 1278 for the user to select from the first and second pairs. When "1" is selected, a PW1 field 1276 displays a given value, or allows the user to enter a value, of the pulse width (e.g., the minimum value of the programmable range), and an AMP1 field 1274 allows the user to enter the value of the amplitude threshold that is associated with the value displayed in PW1 field 1276. When "2" is selected, PW1 field 1276 becomes PW2 field 1276 and displays another given value, or allows the user to enter another value, of the pulse width (e.g., the maximum value of the programmable range), and an AMP1 field 1274 becomes AMP2 field and allows the user to enter the value of the amplitude threshold that is associated with the value displayed in PW2 field 1276. In the illustrated embodiment, the values for the pulse amplitude and the pulse width can be entered by using the "+" and "−" arrows allowing value increase and decrease at predetermined increments, respectively. When entry of the known values of the amplitude threshold for the current stimulation field (FIELD 1 as shown) is completed. An ADDITIONAL FIELD field 1280 allows the user to move to the next field, until the entry of the known values of the amplitude threshold is completed for all the stimulation field used in the pattern of neurostimulation pulses.

FIG. 13 illustrates another embodiment of an area 1370 of the screen of FIG. 12. Area 1370 includes all the features of area 1270 except for including an AMPLITUDE LIMITS area 1372 that differs from AMPLITUDE LIMITS area 1272 by having an ADDITIONAL AMP-PW field 1378 instead of AMP-PW PAIRS field 1278. ADDITIONAL AMP-PW field 1378 allows the user to enter one pair of values of the amplitude threshold and the pulse width at a time until the entry of the known values of the amplitude threshold is completed for all the stimulation field used in the pattern of neurostimulation pulses.

Figure 14:
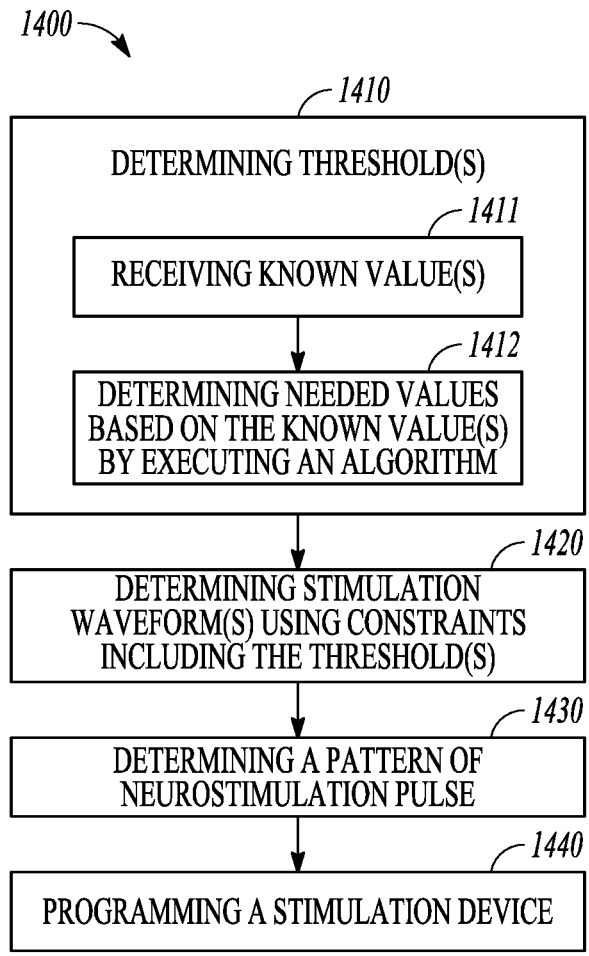
FIG. 14 illustrates an embodiment of a method for programming neurostimulation including determination and use of one or more thresholds.

FIG. 14 illustrates an embodiment of a method 1400 for programming neurostimulation including determination and use of one or more thresholds. Method 1400 can be performed using system 960. In one embodiment, system 960, including but not limited to its various embodiments discussed in this document, can be configured (e.g., programmed) to perform method 1400. In various embodiments, method 1400 is applied for programming a stimulation device, such as stimulation device 104, including but not limited to its various embodiments discussed in this document, to deliver the neurostimulation to tissue of a patient through a plurality of electrodes and to control the delivery of the neurostimulation by the user.

At 1410, one or more thresholds are determined. The one or more thresholds are each a limit for a parameter of waveform parameters defining one or more stimulation waveforms. Examples for the waveform parameters include parameters (1)-(6) as discussed above, and examples for the one or more thresholds include thresholds (A) and (B) as discussed above. The determination includes receiving one or more known values of one or more thresholds at 1411 and determining needed values of the one or more thresholds at 1412.

At 1411, the one or more known values of one or more thresholds are received. In various embodiments, the one or more known values of one or more thresholds can be obtained by measuring from the patient. At 1412, the needed values of the one or more thresholds are determined by executing an algorithm allowing for prediction of the needed values of the one or more thresholds based on the one or more known values.

At 1420, the one or more stimulation waveforms are determined using constraints including the determined one or more thresholds. In various embodiments, the constraints are applied to ensure safety and/or comfort of the patient. For example, the one or more thresholds can be used to prevent intolerable pain and/or other discomfort from being caused by the neurostimulation. In various embodiment, one or more stimulation fields are determined. The one or more stimulation fields are each defined by a set of active electrodes through which one or more neurostimulation pulses will be delivered to the patient. The one or more threshold can be determined for each of the one or more stimulation fields. This means receiving the one or more known values of one or more thresholds and determining the needed values of the one or more thresholds for each stimulation field. In various embodiment, the one or more stimulation fields are each further defined by a fractionalization assigning a fraction of the overall current amplitude of a neurostimulation pulse to each electrode of the set of active electrodes. Different stimulation fields can include stimulation fields that have the same set of active electrodes but different fractionalizations.

At 1430, a pattern of neurostimulation pulses is determined. In various embodiments, the pattern of neurostimulation pulses can include the one or more stimulation waveforms. Stimulation field may not be needed for defining the pattern of neurostimulation pulses when the electrode configuration including fractionalization does not change during the delivery of the neurostimulation according to the pattern of neurostimulation pulses. In various embodiments, the pattern of neurostimulation pulses can include the one or more stimulation waveforms and the one or more stimulation fields.

At 1440, the stimulation device is programmed for delivering the neurostimulation according to the determined pattern of neurostimulation pulses. This can include determining stimulation parameters used by the stimulation device to control the delivery based on the pattern of neurostimulation pulses, and transmitting the stimulation parameters to the stimulation device.

In various embodiments, waveform parameters defining the one or more stimulation parameters can include a pulse amplitude and a pulse width. The one or more thresholds can include an amplitude threshold being a maximum value of the pulse amplitude for each given value or range of values of the pulse width. In one embodiment, the amplitude threshold can be determined as the maximum value of the pulse amplitude for a maximum value of the pulse width in each given range of values of the pulse width. In one embodiment, the amplitude threshold can be determined by determining needed values of the amplitude threshold using one or more known values of the amplitude threshold and a relationship between the pulse amplitude and the pulse width. One example of such a relationship includes a strength-duration curve. The strength-duration curve can be determined for each of the one or more stimulation fields using information including data collected from the patient.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation to tissue of a patient using a stimulation device coupled to a plurality of electrodes and controlling the delivery of the neurostimulation by a user, the system comprising:

a programming control circuit configured to program the stimulation device for delivering the neurostimulation according to a pattern of neurostimulation pulses defined by one or more stimulation waveforms; and a stimulation control circuit configured to determine the pattern of neurostimulation pulses with the one or more stimulation waveforms constrained by one or more thresholds each being a limit for a parameter of waveform parameters defining the one or more stimulation waveforms, the one or more thresholds including one or more maximum values each corresponding to a level of an effect of the neurostimulation that is harmful to or unacceptable by the patient, the stimulation control circuit including threshold circuitry configured to receive one or more known values of the one or more thresholds, to identify one or more worst cases from the one or more stimulation waveforms, and to determine needed values of the one or more thresholds for the identified one or more worst cases by executing an algorithm allowing for prediction of the needed values of the one or more thresholds based on the one or more known values.

2. The system of claim 1, wherein the pattern of neurostimulation pulses comprises the one or more stimulation waveforms and one or more stimulation fields each defined by a set of active electrodes through which one or more neurostimulation pulses of the pattern of neurostimulation pulses are delivered to the patient, and the stimulation control circuit comprises waveform composition circuitry configured to determine the one or more stimulation waveforms and the one or more stimulation fields, and the threshold circuitry is further configured to receive the one or more known values of the one or more thresholds for each stimulation field of the one or more stimulation fields and to determine the needed values of the one or more thresholds for the each stimulation field.

3. The system of claim 1, wherein the threshold circuitry is configured to determine one or more thresholds of a first parameter selected from the waveform parameters for one or more given values or one or more value ranges of one or more second parameters selected from the waveform parameters.

4. The system of claim 3, wherein the threshold circuitry is configured to determine the one or more thresholds of the first parameter for one or more worst-case values of the one or more second parameters.

5. The system of claim 4, further comprising a user interface configured to receive one or more user-defined worst cases in the pattern of neurostimulation pulses from the user and determine the one or more worst-case values of the one or more second parameters being one or more values of the one or more second parameters under the received one or more user-defined worst cases.

6. The system of claim 3, wherein the first parameter is a pulse amplitude, the second parameter is a pulse width, and the threshold circuitry comprises amplitude threshold circuitry configured to determine an amplitude threshold of the one or more thresholds, the amplitude threshold being a limit for the pulse amplitude for each given value or value range of the pulse width.

7. The system of claim 6, wherein the amplitude threshold circuitry is configured to determine the amplitude threshold of the one or more thresholds, the amplitude threshold being a maximum value of the pulse amplitude for a maximum value of the pulse width in the each given value range of the pulse width.

8. The system of claim 6, wherein the amplitude threshold circuitry is configured to determine needed values of the amplitude threshold using one or more known values of the amplitude threshold and a relationship between the pulse amplitude and the pulse width, the relationship including a strength-duration curve.

9. The system of claim 1, wherein the stimulation device comprises an implantable stimulation device configured to deliver the neurostimulation and control the delivery of the neurostimulation using a plurality of stimulation parameters, and further comprising a programmer including the programming control circuit and the stimulation control circuit, the programming control circuit configured to generate the plurality of stimulation parameters according to the pattern of neurostimulation pulses and to transmit the plurality of stimulation parameters to the implantable stimulation device.

10. A method for delivering neurostimulation to a patient using a stimulation device coupled to a plurality of electrodes and controlling the delivery of the neurostimulation by a user, the method comprising:
determining one or more thresholds each being a limit for a parameter of waveform parameters defining one or more stimulation waveforms, the one or more thresholds including one or more maximum values each corresponding to a level of an effect of the neurostimulation that is harmful to or unacceptable by the patient, the determination of the one or more thresholds including:
receiving one or more known values of the one or more thresholds;
determining one or more worst cases in the one or more stimulation waveforms;
determining needed values of the one or more thresholds for the one or more worst cases by executing an algorithm allowing for prediction of the needed values of the one or more thresholds based on the one or more known values;
determining the one or more stimulation waveforms using constraints including the determined one or more thresholds;
determining a pattern of neurostimulation pulses including the determined one or more stimulation waveforms; and
programming the stimulation device for delivering the neurostimulation according to the determined pattern of neurostimulation pulses.

11. The method of claim 10, further comprising determining the one or more known values of the one or more thresholds by measuring from the patient.

12. The method of claim 11, further comprising determining the algorithm for the patient using information including data collected from the patient.

13. The method of claim 10, further comprising determining one or more stimulation fields each defined by a set of active electrodes through which one or more neurostimulation pulses of the pattern of neurostimulation pulses are delivered to the patient, the set of active electrodes selected from the plurality of electrodes, wherein receiving the one or more known values of the one or more thresholds comprises receiving the one or more known values of the one or more thresholds for each stimulation field of the one or more stimulation fields, and determining the needed values of the one or more thresholds comprises determining the needed values of the one or more thresholds for the each stimulation field.

14. The method of claim 13, wherein the one or more neurostimulation pulses each have an overall current amplitude, the one or more stimulation fields are each further defined by a fractionalization assigning a fraction of the overall current amplitude to each electrode of the set of active electrodes, and determining the one or more stimulation fields comprises determining the fractionalization for each of the one or more stimulation fields.

15. The method of claim 13, wherein the waveform parameters comprise a pulse amplitude and a pulse width, determining the one or more thresholds comprises determining an amplitude threshold being a maximum value of the pulse amplitude for each given value or range of values of the pulse width.

16. The method of claim 15, wherein determining the amplitude threshold comprises determining the maximum value of the pulse amplitude for a maximum value of the pulse width in the each given range of values of the pulse width.

17. The method of claim 15, wherein determining the amplitude threshold comprises determining needed values of the amplitude threshold using one or more known values of the amplitude threshold and a relationship between the pulse amplitude and the pulse width.

18. The method of claim 17, wherein determining the amplitude threshold comprises determining the needed values of the amplitude threshold using the one or more known values of the amplitude threshold and a strength-duration curve.

19. The method of claim 18, further comprising determining the strength-duration curve for each stimulation field of the one or more stimulation fields using information including data collected from the patient.

20. A non-transitory computer-readable storage medium including instructions, which when executed by a system, cause the system to perform a method for delivering neurostimulation to a patient using a stimulation device coupled to a plurality of electrodes and controlling the delivery of the neurostimulation by a user, the method comprising:
determining one or more thresholds each being a limit for a parameter of waveform parameters defining one or more stimulation waveforms, the one or more thresholds including one or more maximum values each corresponding to a level of an effect of the neurostimulation that is harmful to or unacceptable by the patient, the determination of the one or more thresholds including:
receiving one or more known values of the one or more thresholds;
determining one or more worst cases in the one or more stimulation waveforms;
determining needed values of the one or more thresholds for the one or more worst cases by executing an algorithm allowing for prediction of the needed values of the one or more thresholds based on the one or more known values;
determining the one or more stimulation waveforms using constraints including the determined one or more thresholds;
determining a pattern of neurostimulation pulses including the determined one or more stimulation waveforms; and
programming the stimulating device for delivering the neurostimulation according to the determined pattern of neurostimulation pulses.

* * * * *